United States Patent
Conley

(10) Patent No.: US 7,658,730 B2
(45) Date of Patent: Feb. 9, 2010

(54) ADULT MALE DISPOSABLE INCONTINENCE SYSTEM FOR DISPOSABLE UNDERWEAR

(75) Inventor: N. Sharon Conley, Ormond Beach, FL (US)

(73) Assignee: Avancen, LLC, Ormond Beach, FL (US)

( * ) Notice: Subject to any disclaimer, the term of this patent is extended or adjusted under 35 U.S.C. 154(b) by 248 days.

(21) Appl. No.: 11/118,801

(22) Filed: Apr. 29, 2005

(65) Prior Publication Data

US 2005/0256467 A1    Nov. 17, 2005

Related U.S. Application Data

(60) Provisional application No. 60/567,267, filed on Apr. 30, 2004.

(51) Int. Cl.
*A61F 5/453* (2006.01)

(52) U.S. Cl. ........................ 604/350; 604/349; 604/353; 604/327; 604/385.09

(58) Field of Classification Search ......... 604/349–353, 604/327, 373, 385.09
See application file for complete search history.

(56) References Cited

U.S. PATENT DOCUMENTS

| | | | | |
|---|---|---|---|---|
| 3,161,198 A | * | 12/1964 | Moxley | 604/353 |
| 3,356,091 A | * | 12/1967 | Patterson | 604/348 |
| 3,405,714 A | * | 10/1968 | Moss | 604/350 |
| 3,526,227 A | * | 9/1970 | Appelbaum | 604/350 |
| 3,901,235 A | * | 8/1975 | Patel et al. | 604/323 |
| 4,022,213 A | * | 5/1977 | Stein | 604/350 |
| 4,553,968 A | * | 11/1985 | Komis | 604/349 |
| 4,568,340 A | * | 2/1986 | Giacalone | 604/353 |
| 4,588,397 A | * | 5/1986 | Giacalone | 604/349 |
| 4,601,716 A | * | 7/1986 | Smith | 604/349 |
| 4,713,066 A | * | 12/1987 | Komis | 604/353 |
| 4,820,291 A | * | 4/1989 | Terauchi et al. | 604/349 |
| 4,994,051 A | * | 2/1991 | Walsh | 604/349 |
| 5,009,649 A | | 4/1991 | Goulter et al. | |
| 5,318,550 A | * | 6/1994 | Cermak et al. | 604/349 |
| 5,380,312 A | * | 1/1995 | Goulter | 604/352 |
| 5,409,475 A | * | 4/1995 | Steer | 604/353 |
| 5,462,539 A | * | 10/1995 | Herman et al. | 604/385.25 |
| 5,555,847 A | * | 9/1996 | Kelly | 119/850 |
| 5,556,393 A | | 9/1996 | Ronnberg | |
| 5,618,277 A | * | 4/1997 | Goulter | 604/349 |
| 5,649,913 A | * | 7/1997 | Cohen | 604/353 |
| 5,792,132 A | * | 8/1998 | Garcia | 604/385.01 |

(Continued)

OTHER PUBLICATIONS www.arcusmedical.com; "Afex Incontinence Management System"; Nov. 14, 2005.

*Primary Examiner*—Tatyana Zalukaeva
*Assistant Examiner*—Paula L Craig
(74) *Attorney, Agent, or Firm*—John L. DeAngelis; Beusse Wolter Sanks Mora & Maire, P.A.

(57) ABSTRACT

An external male urine collection device is inserted into a front opening of a disposable nonwoven diaper or brief. The device comprises a resilient ring for receiving and restraining the penis in a funnel-shaped collection assembly bag extending from the diaper or brief. A distal funnel-like end of the collection bag is attached to a one-way valve and tube assembly to direct the urine from the bag. The tube is attached to a bedside urine storage bag or leg bag.

13 Claims, 3 Drawing Sheets

U.S. PATENT DOCUMENTS

| | | | |
|---|---|---|---|
| 5,855,206 A * | 1/1999 | Ireland | 128/844 |
| 5,984,910 A * | 11/1999 | Berke | 604/352 |
| 6,007,524 A * | 12/1999 | Schneider | 604/327 |
| 6,059,762 A * | 5/2000 | Boyer et al. | 604/349 |
| 6,061,840 A * | 5/2000 | Alligator | 2/403 |
| 6,113,582 A * | 9/2000 | Dwork | 604/349 |
| 6,248,096 B1 * | 6/2001 | Dwork et al. | 604/349 |
| 6,635,038 B2 * | 10/2003 | Scovel | 604/353 |
| 6,682,511 B2 * | 1/2004 | Besoyan | 604/353 |
| 6,817,992 B1 * | 11/2004 | Sassak et al. | 604/385.09 |
| 6,878,138 B2 * | 4/2005 | Tsuji et al. | 604/385.09 |
| 7,192,424 B2 * | 3/2007 | Cooper | 604/544 |
| 2003/0028161 A1 * | 2/2003 | Carballo | 604/349 |

* cited by examiner

ADULT MALE DISPOSABLE INCONTINENCE SYSTEM FOR DISPOSABLE UNDERWEAR

The present application claims the benefit under Section 119(e) of the provisional application filed on Apr. 30, 2004, and assigned application No. 60/567,267.

FIELD OF THE INVENTION

The present invention relates generally to disposable incontinence systems and more specifically to adult male disposable incontinence systems for disposable underwear.

BACKGROUND OF THE INVENTION

Urinary incontinence is defined as the loss of bladder control permitting urine to inadvertently leak from the bladder. It has been estimated that up to 35% of noninstitutionalized elders are incontinent and greater than 50% of nursing home occupants are incontinent of urine.

Urinary incontinence is a costly medical problem both in health care costs and poor patient outcomes. Annually, millions of health dollars are spent to diagnose the causes of incontinence and to provide medical treatment either with medications, surgery and/or various known devices. Disposable underwear partially absorbs the urine and is commonly used to maintain some semblance of hygiene. In spite of the use of disposable underwear, clothes and bed linens require more frequent laundering as they are frequently soaked through wetting. Due to the incontinence, the patient's skin is frequently wet, in an acid environment, resulting in skin breakdown and its complications in bedridden and institutionalized individuals.

Frequently due to caregiver frustration with the effects of incontinence and the lack of a reliable urine external collection system, indwelling tubes are placed into the bladder (i.e. a foley catheter). These indwelling bladder catheters inevitably become colonized with bacteria causing frequent infections that are often life threatening in elderly or disabled patients.

Disposable diapers and briefs/underwear are the most common solution to urinary incontinence in the general population as well as hospitalized and institutionalized patients.

External male urine collection systems are infrequently used because the currently available systems are prone to detachment and wetting. These devices are generally ineffective and uncomfortable for the wearer. No external male urine collection system is sufficiently reliable to allow its use for multiple hours without falling off or becoming increasingly uncomfortable for the wearer.

The most common external collection device used (or attempted) for hospitalized patients is the external condom catheter, comprising a tube connected to an end of a condom collection unit that is attached to the penis with an adhesive or pressure band (i.e. commonly referred to as a "Texas catheter"). The collection unit rarely functions properly because the penis constantly changes size during the day and the condom collection assembly falls off, wasting caregiver time and institutional monies. A dry genital area cannot be maintained when the condom is displaced from its initial position and therefore leaks urine from the collection unit. Another approach maintains the condom collection unit in place with an elastic belt that fits around the patient's waist and/or legs. Force exerted by the elastic retains the collection unit in place.

A variation of the condom catheter is an adhesive unit that fits around only a tip of the penis, i.e. only around the glans penis. This collection assembly is directly connected to a collection bag and tubing to direct the fluid away from the patient. This approach is problematic for long term use because of the risk of skin breakdown with the daily use of an adhesive and the difficulty in maintaining adherence to the glans penis when the penis size contracts and the penis retracts.

Another urine collection approach comprises a custom brief further comprising a condom-like catheter disposed within a pocket formed in the brief. The urine exits the condom catheter into a collection bag. This unit is expensive and, like the other condom-type units described above, fails when the penis contracts.

Due to the various described disadvantages for the catheter-type urine collection systems, a disposable brief or underwear made from a non-woven material is therefore the most common approach for managing urinary incontinence, as well as fecal incontinence. However, in spite of its high absorbency properties the diaper or brief eventually becomes wet. Long periods in wet underwear cause skin breakdown and multiple other ensuing complications. There is therefore a need for a comfortable, reliable, disposable external urine collection system.

BRIEF SUMMARY OF THE INVENTION

According to one embodiment, the present invention comprises a male urine collection apparatus for attachment to an opening defined in an underwear garment or diaper. The collection apparatus comprises a penis restraining ring disposed in the opening for receiving and restraining a penis; a urine assembly collection bag wherein the penis extends into the urine assembly collection bag from the ring and wherein the urine assembly collection bag receives urine released from the penis and a tube affixed proximate a drain region of the urine assembly collection bag for receiving urine from the urine assembly collection bag.

BRIEF DESCRIPTION OF THE DRAWINGS

The present invention can be more easily understood and the advantages and uses thereof more readily apparent when the following detailed description of the present invention is read in conjunction with the figures wherein.

In accordance with common practice, the various described device features are not drawn to scale, but are drawn to emphasize specific features relevant to the invention. Reference characters denote like elements throughout the figures and text.

DETAILED DESCRIPTION OF THE INVENTION

Figure 1:
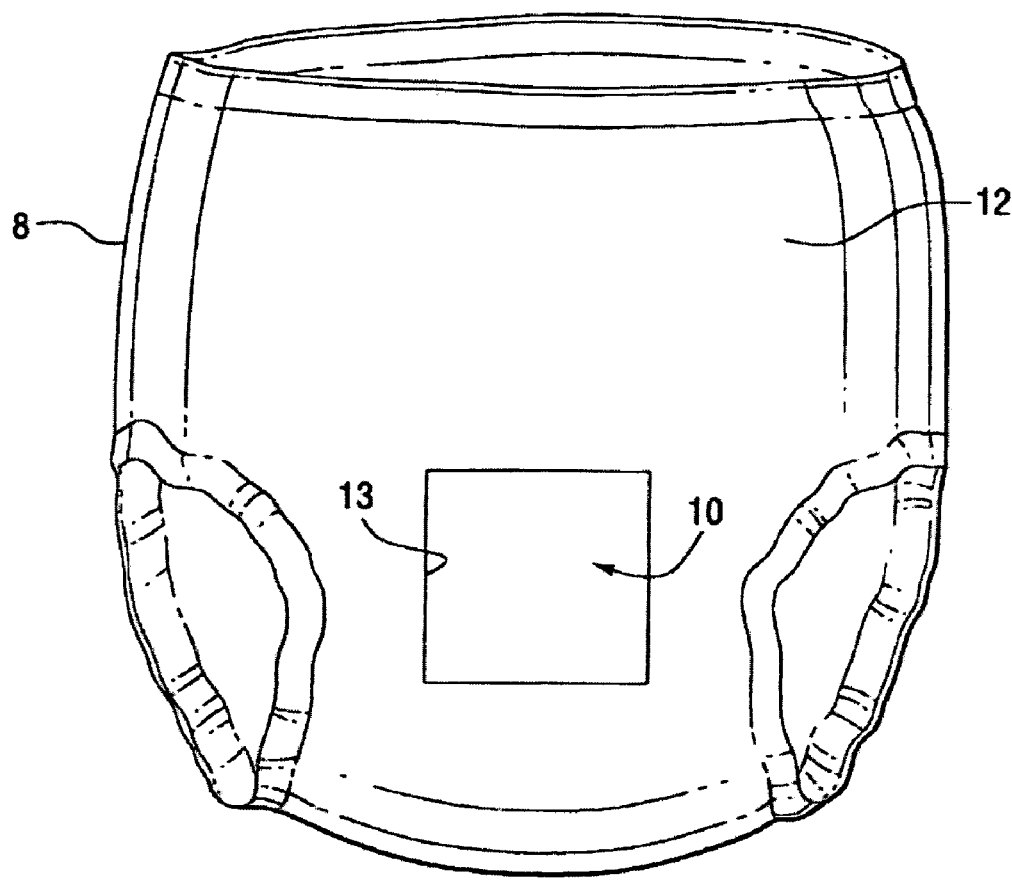
FIG. 1 illustrates a diaper or brief comprising a tear-out region for use with a urine collection system.

Before describing in detail the particular method and apparatus related to an adult male disposable incontinence system, it should be observed that the present invention resides primarily in a novel and non-obvious combination of elements and process steps. So as not to obscure the disclosure with details that will be readily apparent to those skilled in the art, certain conventional elements and steps have been presented with lesser detail, while the drawings and the specification describe in greater detail other elements and steps pertinent to understanding the invention.

The collection system of the present invention will not fall off the penis, a significant deficiency of the prior art devices, as it is incorporated into a disposable diaper or brief according to a preferred embodiment. Specifically, the system of the present invention mates with an opening formed in a front region of a disposable diaper or brief. According to one embodiment, the opening is formed by removing a removable tear-out segment disposed in the front region. The diaper or brief can be constructed with the tear-out segment formed therein, for easy removal and installation of the collection system or the diaper or brief can be fabricated with the collection system of the present invention affixed thereto.

The collection system can be worn for multiple hours and maintains a dry disposable brief, since the urine is diverted away from the diaper or brief into a collection bag. This feature allows one to wear the disposable brief for longer periods, until the diaper or brief is soiled by usual wear or fecal incontinence. The system of the present invention maintains a dry skin condition since the urine is diverted away from the diaper or brief. According to one embodiment, the urine collection system is disposable, allowing a patient to enjoy a clean disposable diaper and clean urine collection device.

The external collection assembly of the present invention mates with an opening formed in a disposable diaper or brief. The urine collection system comprises an elastic or resilient penis sleeve or ring that holds the penis in place within a comfortable assembly collection bag attached to the diaper. The size of a sleeve opening varies to accommodate the penis as it changes size throughout the day, preventing the penis from separating from the collection system. Urine collects at the bottom of the funnel-shaped assembly collection bag attached to the diaper, and is immediately directed away from the diaper or brief through a one-way flow valve into a common urine collection tube and a bedside or leg bag. The one-way flow valve prevents urine flow in a direction toward the assembly collection bag.

Preferably, a material of the penis sleeve or ring and the assembly collection bag comprises a nonwetable breathable fabric that allows ventilation and promotes drying of any moisture that is not completely drained from the bag. Also, preferably, the entire external urine collection assembly is disposable.

The advantages of the external collection system of the present invention include patient comfort and reliability. The system can be incorporated into a modified disposable diaper or brief by a caregiver or user who lacks medical training. Using the collection device of the present invention promotes a dry genital area, preventing skin breakdown and reducing the need for multiple diaper changes.

As illustrated in FIG. 1, a disposable brief or diaper 8 comprises a pull out, tear-out or removable region 10, in one embodiment having a square shape. Preferably, the tear-out region 10 is disposed in a front surface 12 of the diaper or brief 8, generally positioned in a location proximate the base and the shaft of the male penis when the diaper is worn by an adult male. As described further below, the external urine collection system of the present invention is affixed to and protrudes externally from the removable region 10. In another embodiment, the urine collection system is fabricated with the brief or diaper 8 and thus the brief or diaper 8 is an integral element of the collection system.

Figure 2:
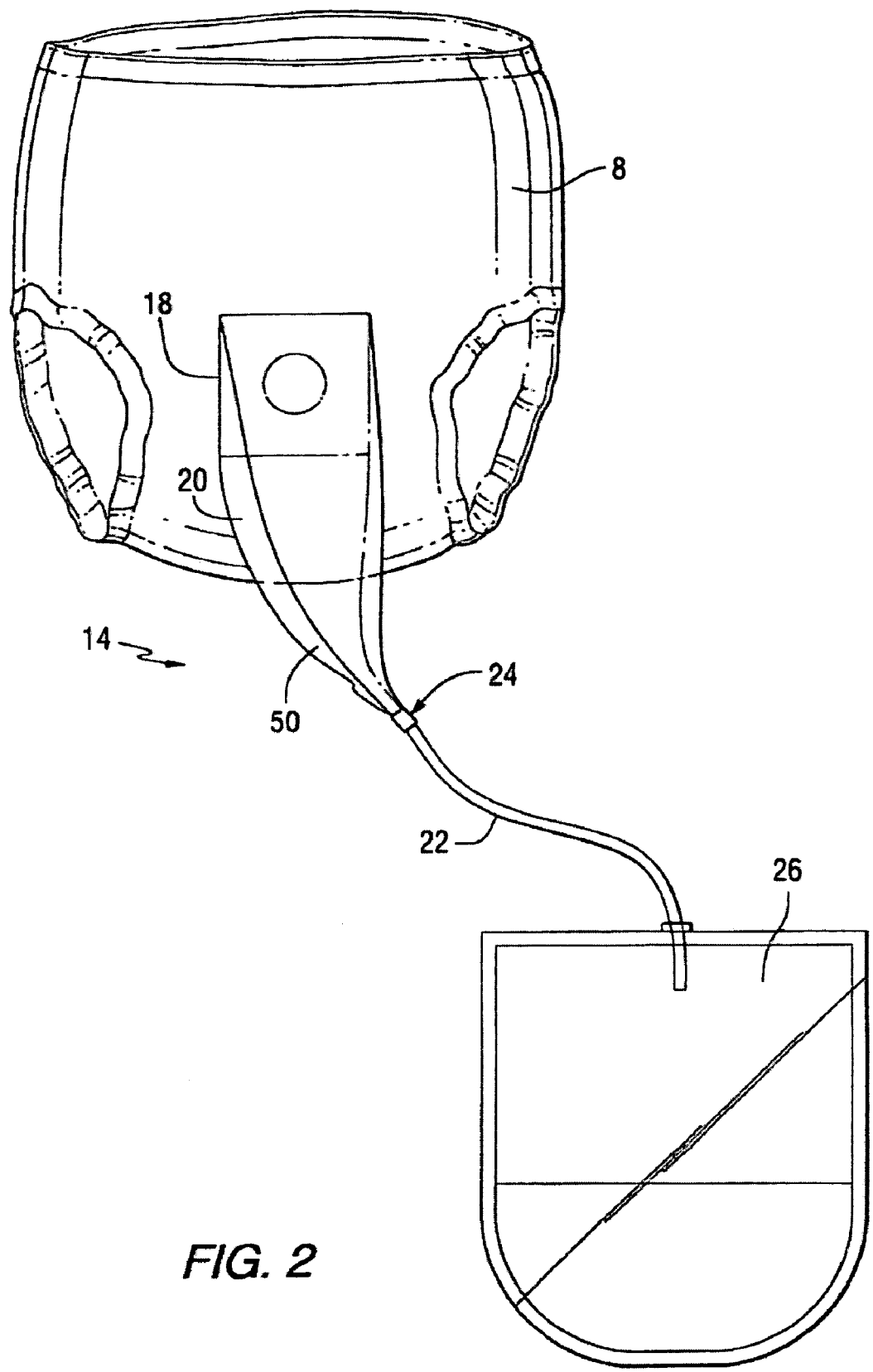
FIG. 2 illustrates a external urine collection system of the present invention.

As illustrated in FIG. 2, a urine collection system 14 of the present invention comprises a penis-holding sleeve or retaining ring 18 for retaining the penis within an assembly collection bag 20. Urine collected in the collection bag 20 flows through a tube 22 via a one-way valve 24 to a urine collection or storage bag 26 or to a leg bag (not illustrated) for ambulatory users. When the brief 8 becomes soiled, it can be removed with the attached incontinence system 14 and a clean brief 8 with a clean attached urine collection system 14 assembled thereto.

Figure 3:
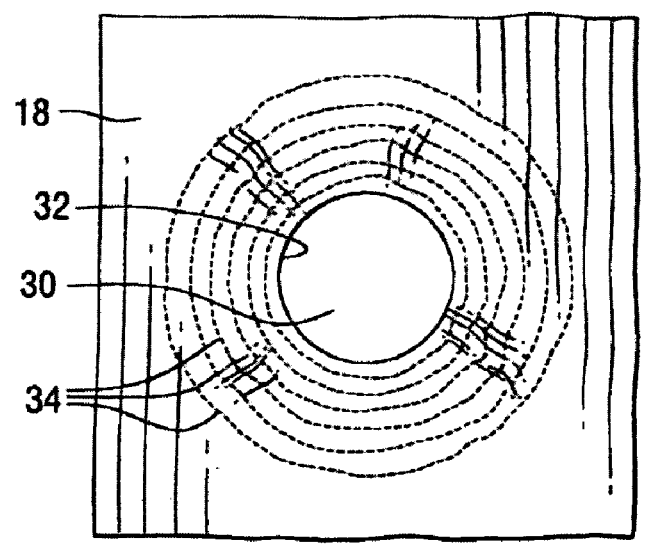
FIG. 3 illustrates a penis entry and holding (restraining) element of the present invention.

A material of the sleeve or ring 18 comprises a resilient material formed from a relatively soft preferably nonwettable and breathable fabric. In one embodiment, the sleeve or ring 18 defines an opening 30 having a diameter of approximately 6 cm. See FIG. 3. A rim 32 of the opening 30 comprises an elastic material or elastic stitching 34 that exerts a radially directed force about the circumference of the penis proximate the penis base, thereby gently restraining the penis within the sleeve or ring 18 and permitting the remaining length of the penis to extend into the collection bag 26. In one embodiment of the present invention, the elastic material or stitching 34 comprises multiple continuous concentric circles of material having an elastic property.

The sleeve or ring 18 circumscribes the penis and exerts the radial force only proximate the penis base. Thus it is capable of restraining the penis within the opening 30 as the size of the penis changes and the elastic sleeve or ring material 34 radially expands or contracts in response thereto to retain the penis within the sleeve or ring 18. In contrast, the prior art discloses condom-like structures that enclose an entire length of the penis and cannot restrain the penis as it changes size.

Figure 4:
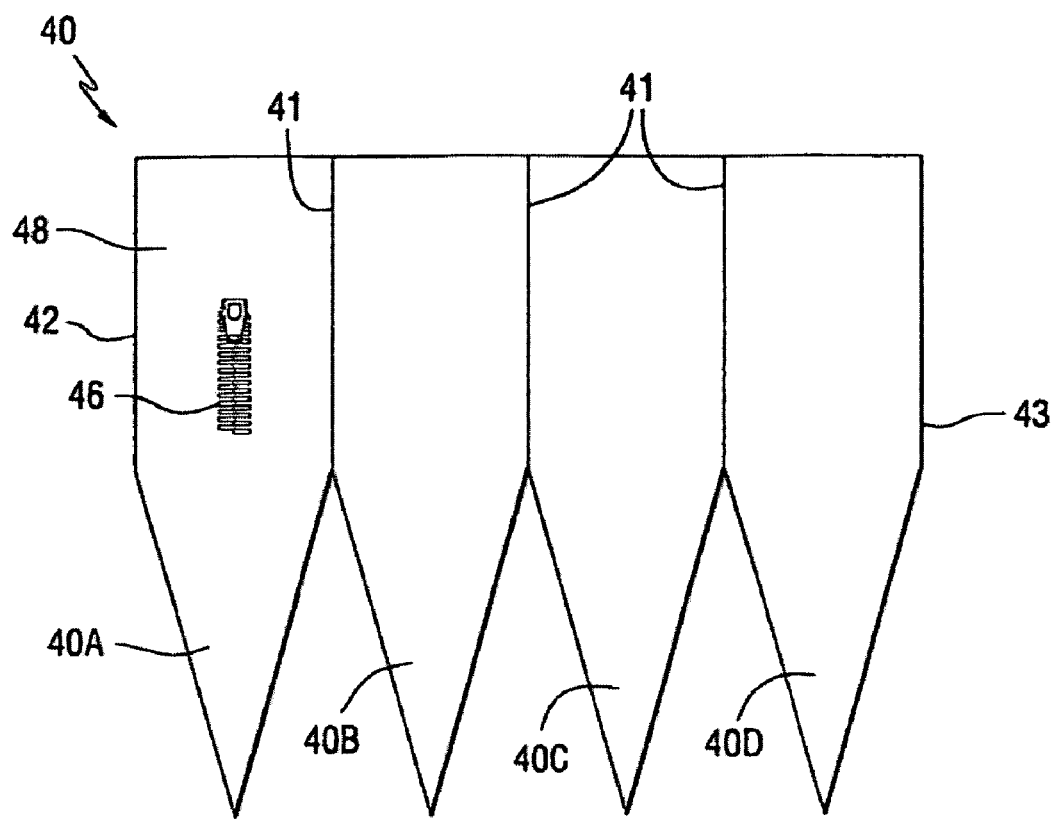
FIG. 4 illustrates a collection bag of the present invention in disassembled form.

With the sleeve or ring 18 exerting the restraining force at the base of the penis, a remaining length of the penis (is disposed within the collection bag 20. In one embodiment, the assembly collection bag 20 (see FIG. 4) is formed from a continuous fabric piece 40 preferably comprising a breathable nonwetable material, such as the same material used for the sleeve or ring 18. Folding the piece 40 along fold lines 41 separating regions 40A, 40B, 40C and 40D and sewing or affixing edges 42 and 43 (using any known attaching or affixing techniques), forms the assembly collection bag 20 having a three-dimensional funnel shape. As can be appreciated by those skilled in the art, other techniques and materials can be employed to form the assembly collection bag 20. A shape of the assembly collection bag can be varied from that presented herein, so long as the shapes promotes urine flow in a direction toward the urine collection bag 26. Depending on the material from which the assembly collection bag 20 is constructed, the material may not accept a stiff fold formed therein, and thus the fold lines 41 instead demail regions 40A, 40B, 40C and 40D of the bag 20.

In one embodiment, the assembly collection bag 20 comprises a zipper 46 disposed in a front surface 48 of the collection bag 20. Use of the zipper 46 and the zippered closure formed thereby allows the caregiver or user to view the penis orientation within the bag 20 and make positional adjustments as necessary. Also, opening the zipper 46 allows the wearer to void normally, if capable, between periods of incontinence.

The assembly collection bag 20 defines an opening therein proximate a drain region 50 (see FIG. 2) for receiving the one-way flow valve 24. In an embodiment in which the collection bag 20 further comprises a funnel-shape, the drain region 50 comprises a distal end of the assembly collection bag 20. The valve 24 comprises appropriate fittings for connection to the tubing 22 and to the collection bag 20. In another embodiment the valve 24 is disposed along the tubing 22 at any location between the assembly collection bag 20 and the urine collection bag 26.

Figure 5:
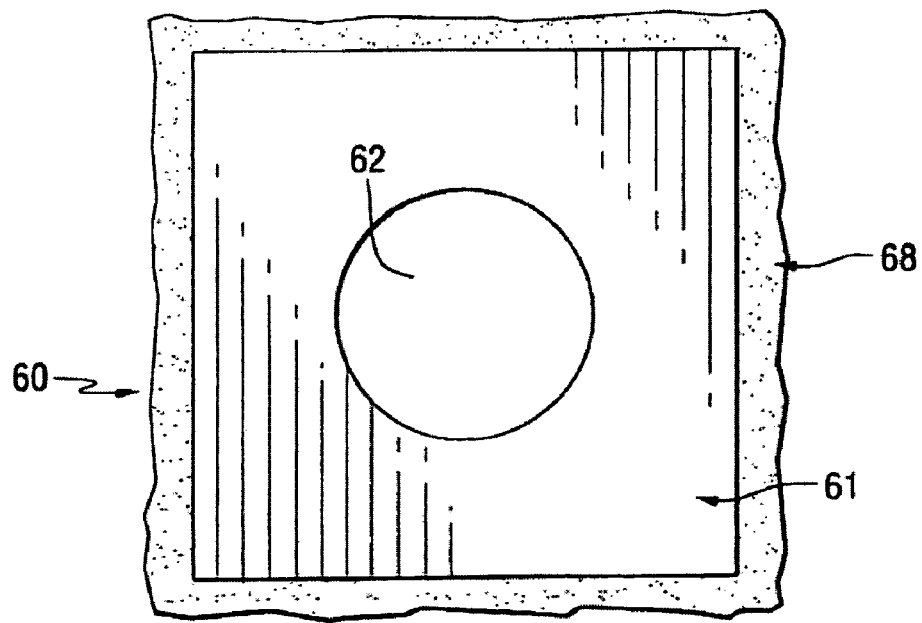
FIG. 5 illustrates a piece assembly of the present invention.

According to one embodiment, the sleeve or ring 18 and the collection bag 20 are affixed to an assembly piece 60 shown in FIG. 5, specifically within a region 61 of the assembly piece 60. The assembly piece 60 provides a rigid framework for receiving the sleeve 18 and the bag 20. The assembly piece 60 is preferably formed from a stiff, soft, nonwetable and breathable material. As shown, the assembly piece 60 defines a 6 cm diameter opening 62 for mating with the sleeve 18 and the opening 30 defined therein. The sleeve 18 is affixed to the assembly piece 60, (by sewing, for example, or by any other known technique) followed by the attachment of the assembly collection bag 20.

According to one assembly technique, the sleeve 18 is disposed over the assembly piece 60 and the assembly collection bag 20 is disposed over the sleeve 18. Both the sleeve 18 and the collection bag 20 are sewn or otherwise attached to the assembly piece 60, such that the sleeve 18 directs the penis into the collection bag 20.

The assembly piece 60 further comprises an adhesive margin 68 (see FIG. 5) disposed along one or more edges thereof for attaching the assembly piece 68 to the disposable brief. To attach the assembly piece 60 to the brief or diaper 8, the assembly piece 60 with the sleeve 18 and the assembly collection bag 20 connected thereto are placed into the opening 10 (see FIG. 1) and affixed to an inside surface of an opening edge 13 by disposing the adhesive margin 68 along the edge 13 and applying a force to adhere the adhesive margin to the inside surface. Typically, the adhesive margin 68 comprises a pull-off adhesive cover that is removed to expose the adhesive margin and to permit attachment of the assembly piece 60 to the brief 8, with the adhesive material providing sufficient force to hold the assembly piece 60 within the diaper 8. Thus the sleeve 18 and the assembly collection bag 20 extend from the brief 8 with a sealed joint formed between the brief 8 and the assembly piece 60, thereby minimizing urine leakage or seepage to an interior surface of the brief 8.

Those skilled in the art recognize that other assembly techniques and structures can be employed to assemble the sleeve 18, the collection bag 20 and the brief 8, with or without use of the assembly piece 60. Such techniques and structures are considered within the scope of the present invention, and preferably form seals between the various elements that minimize the leakage or seepage of urine back to the brief 8, especially minimizing the leakage or seepage of urine to an interior surface of the brief 8.

According to one embodiment, the various elements of the collection system 14 are disposable. After a period of use they are discarded with the disposable brief. The urine collection system 14 can remain in place for many hours collecting multiple episodes of urine release from the penis. Once the briefs are soiled or there is a desire for a clean brief with a new urine collection assembly, the brief 8 and the assembly 14 are discarded and replaced with a fresh brief and urine collection system 14.

While the present invention has been described with reference to preferred embodiments, it will be understood by those skilled in the art that various changes may be made and equivalent elements may be substituted for the elements thereof without departing from the scope of the invention. The scope of the present invention further includes any combination of elements from the various embodiments set forth herein. In addition, modifications may be made to adapt a particular situation to the teachings of the present invention without departing from its essential scope. Therefore, it is intended that the invention not be limited to the particular embodiments disclosed, but that the invention will include all embodiments falling within the scope of the appended claims.

What is claimed is:

1. A male urine collection apparatus for attaching to a first opening defined an underwear garment or diaper, the collection apparatus extending externally from the underwear garment or diaper, the collection apparatus comprising:
   a planar substantially rigid assembly element mounted to an inside surface of the underwear garment or diaper and defining a second opening aligned with the first opening;
   a penis restraining elastic ring disposed within the second opening for receiving and restraining a penis by exerting a radially-directed restraining force about a penis circumference at a penis base, the elastic ring comprising a plurality of multiple continuous closely spaced circles of material having an elastic property, said multiple continuous closely spaced circles being dimensioned and configured to radially expand and contract as a penis radius varies throughout a day, the elastic ring and the radially-directed force substantially limited to a plane of the planar assembly element;
   a urine collection bag larger than the penis, wherein the radially-directed restraining force about the penis circumference at the penis base exerted by the elastic ring permits the length of the penis to extend into the urine collection bag from the ring, and wherein the penis is free to move within the urine collection bag and the collection bag is configured to exert substantially no restraining force about the penis circumference along a penis length, and wherein the urine collection bag is configured to receive urine released from the penis; and
   a tube affixed proximate a drain region of the urine collection bag for receiving urine from the urine collection bag; wherein
   the urine collection bag comprises a first urine collection bag affixed to a first end of the urine tube, the first urine collection bag being a shaped urine collection bag for directing the urine away from the underwear garment, and the apparatus further comprises a second urine collection bag affixed to a second end of the tube for receiving urine from the first urine collection bag through the tube;
   further comprising a one-way flow valve disposed intermediate the first urine collection bag and the second urine collection bag for preventing urine flow in a direction toward the first urine collection bag.

2. The apparatus of claim 1 wherein the urine collection bag further comprises a closable opening for providing access to the penis.

3. The apparatus of claim 2 wherein the closable opening comprises a zippered opening.

4. The apparatus of claim 1 wherein the shaped urine collection bag comprises a funnel-shaped urine collection bag, and wherein the drain region comprises a drain end of the funnel-shaped urine collection bag.

5. The apparatus of claim 1 wherein the second urine collection bag comprises a bed-mounted or a leg-mounted urine collection bag.

6. The apparatus of claim 1 wherein the planar assembly element further comprises an adhesive material disposed proximate one or more edges thereof for detachably mounting the planar assembly element to the inside surface of the underwear garment or diaper to form a joint limiting urine seepage to an interior surface of the underwear garment or diaper.

7. The apparatus of claim 1 wherein the drain region of the urine collection bag comprises a distal end of the urine collection bag.

8. A male urine collection apparatus comprising:
   an underwear garment, the underwear garment defining a first opening in a front surface of the underwear garment;
   a planar substantially rigid assembly element mounted to an inside surface of the underwear garment, the assembly element defining a second opening aligned with the first opening.
   a penis restraining elastic ring disposed within the second opening, the elastic ring being disposed in the front surface of the underwear garment, the elastic ring defining an opening therein, the elastic ring exerting a radially-directed restraining force about a penis circumference at a penis base, the elastic ring comprising a plurality of multiple continuous closely spaced circles of material having an elastic property, said multiple continuous closely spaced circles being dimensioned and configured to radially expand and contract as a penis radius varies throughout a day, the elastic ring and the radially-directed force substantially limited to the penis base;
   a urine collection bag larger than the penis affixed to the ring or to the underwear garment and extending outwardly from the underwear garment, wherein a penis is received within the opening and restrained by the elastic restraining ring, and wherein a free end of the penis further extends into the collection bag and the collection bag exerts is configured to exert no restraining force about the penis circumference along a penis length; and
   a urine tube affixed proximate a drain region of the urine collection bag for receiving urine from and directing urine away from the urine collection further comprising a one-way flow valve disposed intermediate the first urine collection bag and the second urine collection bag for preventing urine flow in a direction toward the first urine collection bag.

9. The apparatus of claim 8 wherein the urine collection bag further comprises a closable opening for providing access to the penis.

10. The apparatus of claim 8 wherein the closable opening comprises a zippered opening.

11. The apparatus of claim 8 wherein the second urine collection bag comprises a bed-mounted or leg mounted urine collection bag.

12. The apparatus of claim 8 wherein the underwear garment comprises an underwear brief or a diaper.

13. A male urine collection apparatus having a first end adapted for attaching to a first opening defined in an underwear garment or diaper, the collection apparatus comprising:
   a planar substantially rigid assembly element mounted to an inside surface of the underwear garment or diaper and defining a second opening aligned with the first opening;
   a penis restraining elastic ring disposed in the second opening and for exerting a radially-directed restraining force about a penis circumference at a penis base, the elastic ring and the radially-directed force substantially limited to a plane of the planar assembly element;
   a urine collection bag extending from the ring, the ring being dimensioned and configured for receiving and restraining a penis as the penis size changes throughout a day, wherein the penis extends through the ring into the urine collection bag and is free to move within the urine collection bag, the collection bag being configured to exert substantially no restraining force about the penis circumference along the penis length, the urine collection bag being adapted for connecting to a urine storage bag such that urine released from the penis is collected by the urine collection bag and directed to the urine storage bag; wherein
   the elastic ring comprises a plurality of multiple continuous closely spaced circles of material having an elastic property, the multiple continuous closely spaced circles being dimensioned and configured to radially expand and contract as a penis radius varies throughout a day;
   further comprising a one-way flow valve disposed intermediate the urine collection bag and the urine storage bag for preventing urine flow in a direction toward the urine collection bag.

* * * * *